United States Patent [19]

Drent

[11] Patent Number: 5,304,674
[45] Date of Patent: Apr. 19, 1994

[54] PREPARATION OF ALKANEDIOIC DERIVATIVES

[75] Inventor: Eit Drent, Amsterdam, Netherlands

[73] Assignee: Shell Oil Company, Houston, Tex.

[21] Appl. No.: 82,212

[22] Filed: Jun. 24, 1993

[30] Foreign Application Priority Data

Jun. 29, 1992 [EP] European Pat. Off. ......... 92201942.7

[51] Int. Cl.$^5$ .................. C07C 67/39; C07C 51/14
[52] U.S. Cl. ...................... 560/204; 562/522
[58] Field of Search ............ 562/522; 560/204

[56] References Cited

U.S. PATENT DOCUMENTS

| | | | |
|---|---|---|---|
| 4,691,047 | 9/1987 | Drent | 560/204 |
| 4,861,912 | 8/1989 | Drent et al. | 560/204 |
| 5,028,734 | 7/1991 | Drent | 560/207 |

*Primary Examiner*—José G. Dees
*Assistant Examiner*—Joseph M. Conrad, III

[57] ABSTRACT

The invention relates to a direct process for the preparation of alkanedioic derivatives, for example alkanedioic diesters, by reaction of an aliphatic conjugated diene such as butadiene with carbon monoxide and a hydroxyl group-containing compound such as a $C_{1-6}$ alkanol in the presence of a catalyst system containing a) a source of cationic palladium,
b) a first bidentate diphosphine ligand having electron-withdrawing substituents on the phosphorus atoms,
c) a second bidentate diphosphine ligand having electron-releasing substituents on the phosphorus atoms, and
d) a source of an anion.

9 Claims, No Drawings

PREPARATION OF ALKANEDIOIC DERIVATIVES

FIELD OF THE INVENTION

This invention relates to the preparation of alkanedioic derivatives. In one aspect, the invention relates to an improved process to prepare alkanedioic derivatives by the reaction of an aliphatic conjugated diene with carbon monoxide and a hydroxyl group-containing compound.

BACKGROUND OF THE INVENTION

It is known that conjugated dienes can be carbonylated using various palladium catalysts. Depending on the nature of the hydroxyl group-containing compound used as coreactant various alkanedioic derivatives can be obtained. For example, carboxylic acid esters will be obtained in the presence of alcohols, carboxylic acids in the presence of water, and carboxylic anhydrides in the presence of carboxylic acids.

While dienes have two double bonds potentially available for carbonylation, most of the known processes result in the carbonylation of only one of these double bonds and forms monofunctional alkenoic derivatives. For the production of difunctional derivatives, it is required to isolate this alkenoic intermediate product and to subject it to carbonylation of its remaining double bond in a separate step.

Thus, U.S. Pat. No. 4,861,912 discloses a two-step process for the preparation of adipic acid or esters. In U.S. Pat. No. 4,861,912, 1,3-butadiene is carbonylated using a catalyst system containing a palladium compound and a bidentate diphosphine ligand having aromatic substituents on the phosphorus atoms in a first step forming a pentenoic acid or ester, subsequently isolating the pentenoic acid or ester obtained, followed by carbonylating the isolated pentenoic acid or ester in the presence of a second carbonylation catalyst. The requirement of isolation of the intermediate product makes this known process more laborious.

U.S. Pat. No. 4,691,047 discloses a process for the direct conversion of conjugated diene into carboxylic diacids or diesters using a catalyst system containing a palladium compound, an aryl-substituted monophosphine, optionally in conjunction with an aryl-substituted bidentate diphosphine, and at least one mole of hydrogen chloride per atom of trivalent phosphorus present in the catalytic system. Due to the corrosive nature of hydrogen chloride, this known process suffers from severe equipment requirements when being conducted on an industrial scale. Also, the monophosphine component of this catalyst system tends to become inactivated under the conditions applied.

It is therefore an object of the present invention to provide an improved direct process to prepare alkanedioic derivatives by the reaction of an aliphatic conjugated diene with carbon monoxide and a hydroxyl group-containing compound.

SUMMARY OF THE INVENTION

According to the present invention a process to prepare alkanedioic derivatives is provided comprising reacting an aliphatic conjugated diene with carbon monoxide and a hydroxyl group-containing compound in the presence of a catalyst system comprising:
a) a source of cationic palladium,
b) a first bidentate diphosphine ligand having electron-withdrawing substituents on the phosphorus atoms,
c) a second bidentate diphosphine ligand having electron-releasing substituents on the phosphorus atoms, and
d) a source of an anion.

DETAILED DESCRIPTION OF THE INVENTION

It has now been found that alkanedioic derivatives can directly be obtained from readily available diene feedstock under mild conditions using a non-corrosive catalyst system of the invention. The non-corrosive catalyst system contains a) a source of cationic palladium, b) a first bidentate diphosphine ligand having electron-withdrawing substituents on the phosphorus atoms, c) a second bidentate diphosphine ligand having electron-releasing substituents on the phosphorus atoms, and d) a source of an anion.

The process of the invention is advantageous in providing a direct route to alkanedioic derivatives, such as adipate esters, as shown in the below examples. Further, the catalyst system used in the process have improved stability.

As used herein, the term "conjugated diene" refers to dienes having at least two double bonds which alternate with single bonds such as, for example, 1,3-butadiene, 1,3-pentadiene, 1,3-hexadiene, 1,3-cyclohexadiene, 2,4-heptadiene, 2-methyl-1,3-butadiene, and the like. By being aliphatic "conjugated dienes", multienes having aromatically delocalized double bonds as the sole conjugated multiene segment are excluded from the scope of the present invention. However, the aliphatic conjugated dienes may have non-aliphatic groups, such as phenyl groups, substituted onto the —C=C—C=C— backbone.

The hydroxyl group-containing compound used in the present process may be an alcohol, or a carboxylic acid or water. Accordingly, alkanedioic diesters, dianhydrides and diacids may be obtained by the present process. Preferably, the hydroxyl group-containing compound is an alcohol, more preferably an alkanol, and most preferably an alkanol having from to 6 carbon atoms. Typical examples of preferable alcohols include methanol, ethanol, n-propanol, isopropanol, butanols, and polyhydric alcohols such as ethylene glycol and 1,3-propanediol, which result in polyesters being produced.

The palladium catalyst used in the process of the invention may be provided in the form of a palladium complex of one or both of the specified diphosphines. It may also conveniently be generated in situ by adding a source of palladium and sources of the diphosphines to the reaction. Suitable sources of palladium include palladium carboxylates, such as palladium acetate, propionate, butyrate or benzoate, and palladium salts of mineral acids. Further sources include palladium complexes such as palladium acetylacetonate, tetrakis(triphenylphosphine)palladium and bis(tri-otolylphosphine)palladium acetate. Preferably the source of palladium is free of halide. Palladium may be used in a heterogeneous form such as, for example, loaded on an ion exchange resin.

It is a characteristic feature of the present invention that the catalyst system contains a combination of at least two bidentate diphosphine ligands, which are distinguished by having electron withdrawing and electron releasing substituents on the phosphorus atoms, respectively.

Preferably, the first bidentate diphosphine ligands have aromatic substituents. More preferably, the first bidentate diphosphine ligand is a diphosphine of formula:

$$R^1R^2{>}P{-}R{-}P{<}R^3R^4 \quad \quad (I),$$

wherein $R^1$, $R^2$, $R^3$ and $R^4$ independently represent optionally substituted aryl groups, and R represents a bridging group having at least two carbon atoms in the bridge. The substituents on the aryl groups can be any inert substituent that does not interfere with the reaction such as alkyl, aryl, alkoxy or halide groups. Typical aryl groups represented by $R^1$, $R^2$, $R^3$, $R^4$ include phenyl, naphthyl, o-methoxyphenyl, p-tolyl, o-tolyl, m-chlorophenyl and p-chlorophenyl.

Preferably, the second bidentate diphosphine ligands have aliphatic substituents. More preferably, the second bidentate diphosphine ligand is a diphosphine of formula:

$$R^5R^6{>}P{-}R{-}P{<}R^7R^8 \quad \quad (II),$$

wherein $R^5$, $R^6$, $R^7$ and $R^8$ independently represent optionally substituted aliphatic groups, and R represents a bridging group having at least two carbon atoms in the bridge. The optionally substituted aliphatic groups may be monovalent or divalent, in the latter case being bonded to a single or to both phosphorus atoms of the diphosphine ligand. Suitable aliphatic groups particularly include unsubstituted optionally branched or cyclic alkyl or alkylene groups having from 1 to 10 carbon atoms, more preferably from 1 to 6 carbon atoms. Preferably, $R^5$, $R^6$, $R^7$ and $R^8$ independently are selected from the group of alkyl, alkylene, cycloalkyl and cycloalkylene groups. Typical examples of aliphatic groups $R^5$, $R^6$, $R^7$ and $R^8$ include methyl, ethyl, propyl, isopropyl, n-butyl, s-butyl, t-butyl, cyclohexyl, pentamethylene, hexamethylene and cyclooctylene.

For being capable of bidentate coordination to the palladium atom, the bidentate diphosphine ligands of the catalyst system should be free of substituents offering stearic hindrance to a bidentate coordination mode. In particular, the divalent bridging group R should be free of substituents offering stearic hindrance, but otherwise can be any divalent group having two or more carbon atoms and optionally further heteroatoms, such as oxygen or nitrogen in the bridge interconnecting both phosphorus atoms, and any further groups or atoms attached thereto. The bridging group R may make part of a cyclic structure, e.g. an aromatic or cycloaliphatic group, and the bonds in the bridge may be saturated or unsaturated. Also an 3-oxapentamethylene group is suitable. Preferably, the bridging group R is an optionally substituted alkylene group having at least three carbon atoms in the chain, more preferably three or four carbon atoms. The first bidentate diphosphine ligand most preferably has four carbon atoms in the bridge, and the second ligand most preferably has three carbon atoms in the bridge.

Preferable first bidentate diphosphine ligands include, for example, 1,3-bis(diphenylphosphino)propane, 1,4-bis(diphenylphosphino)-butane, 1,3-bis(di-o-methoxyphenylphosphino) propane, 1,4-bis(di-p-chlorophenylphosphino)butane, and 1,4-bis(di-p-tolylphosphino)butane.

Preferable second bidentate diphosphine ligands include, for example, 1,2-bis(di-n-butylphosphino)ethane, 1,3- bis(dimethylphosphino)-propane, 1,3-bis(diethylphosphino)propane, 1,3-bis(di-i-propylphosphino)propane, 1,3-bis(di-npropylphosphino)propane, 1,3-bis(di-i-butylphosphino)propane, 1,3-bis(di-n-butyl-phosphino)-propane, 1,3-bis(di-s-butylphosphino)propane, 1,3-bis(-di-t-butylphosphino)propane, 1,3bis(di-n-hexyl-phosphino)propane, 1,2-bis(dicyclohexylphosphino)ethane, 1,3-bis(n-butylmethylphosphino)propane, 1,3-bis(n-butylethylphosphino)propane, 1,3-bis(1,5-cyclooctylene phosphino)propane and its isomeric mixture containing 1,4-cyclooctylene groups, 1,4-bis(di-i-propylphosphino)butane, 1,5- bis(dimethylphosphino)-3-oxapentane, 1,8-bis(di-n-butylphosphino)-3,6-dioxaoctane, and 1,4-bis(di-n-butylphosphino)2,2,3,3-tetramethylbutane.

The ratio of the number of moles of either of the diphosphines per gram atom of palladium is preferably within the range of from about 0.50 to about 10, more preferably from about 0.9 to about 5, especially from about 1 to about 4. Preferably, the first bidentate diphosphine is used in molar excess relative to the second bidentate diphosphine, a ratio within the range of from about 1:1 to about 10:1 being most preferred.

The source of an anion, used in the process of the invention is preferably a protonic acid However, it may also be a salt of palladium or a salt of another metal such as, for example, of vanadium, chromium, nickel, copper or silver, or the salt of a protonated base when the protonic acid is neutralized with a base such as in 3,4-lutidinium salts. Preferably, the anion is derived from a weak protonic acid, in particular a carboxylic acid, having a pKa greater than 3, measured at 18° C. in aqueous solution, and being sterically hindered. Typically sterically hindered carboxylic acids, from which suitable anions may be derived, include 2,4,6-trimethylbenzoic acid, 2,6dichlorobenzoic acid, 9-anthroic acid, pivalic acid, 1,2,3benzenetricarboxylic acid and its 1,3-diester which may be formed in situ, 2-ethoxy-1-naphthalene carboxylic acid, and 2,6dimethoxybenzoic acid.

The ratio of moles of anions per gram atom of palladium is not critical. Preferably it is within the range of from about 0.5 to about 100, more preferably within the range of from about 1 to about 10.

The diphosphines of formula I as such are known compounds, and can be prepared by general methods described in the literature, for example Houben-Weyl, Vol. XII/I, p.21.

The catalyst system used in the process according to the invention may be homogeneous or heterogeneous. Preferably it is homogeneous, or an immobilized homogeneous catalyst system.

The catalyst system according to the invention is preferably carried out in a liquid phase. The liquid phase may conveniently be formed by one or more of the reactants. Alternatively, it may be formed by a solvent. It may also be formed by one of the components of the catalyst system. Any inert solvent can be used. Such solvent may, for example, contain sulfoxides and sulfones such as, for example, dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, and xylenes; esters such as methyl acetate and butyrolactone; ketones such as acetone or methyl isobutyl ketone; alcohols such as methanol and ethanol; ethers such as tetrahydrofurane (also referred to as THF), anisole, 2,5,8-trioxanonane (also referred to as diglyme), diphenyl ether and diisopropylether; and amides such as dimethylacetamide and Nmethylpyrrolidone. Alcohols may function as coreactant to form esters.

The process according to the invention is conveniently carried out at a temperature within the range of from about 50° C. to about 200° C., in particular from about 100° C. to about 150° C. Higher or lower temperature are not excluded, but usually don't provide any economic advantage.

The process according to the invention is preferably carried out at a total pressure of from about 1 to about 80 bar. Pressures higher than 100 bar may be used, but are generally economically unattractive on account of special apparatus requirements. More preferred pressures are within the range of from about 5 to about 70 bar.

The process according to the invention may be carried out continuously or batchwise. Carbon monoxide grade, reaction equipment and product purification are not critical, and well within the skills of the relevant technician.

ILLUSTRATIVE EMBODIMENT

The invention will be illustrated in further detail by the following non-limiting examples.

EXAMPLE 1

A 300 ml magnetically stirred stainless-steel autoclave was charged with 20 ml ethanol, 40 ml diphenylether, 0.5 mmol palladium acetate, 2 mmol 1,4-bis(diphenylphosphino)butane, 0.6 mmol 1,3-bis(di-ipropylphosphino)propane and 10 mmol 9-anthracene carboxylic acid. The autoclave was flushed and evacuated, whereupon 10 ml of liquid 1,3-butadiene was added, and carbon monoxide introduced to an initial pressure of 40 bar. The autoclave was heated to 150° C. for 15 hours. Upon cooling, the contents of the autoclave were analyzed by gas liquid chromatography (GLC). It was found that 100% of the 1,3-butadiene was converted with a selectivity of 37% into diethyl diesters of $C_6$-alkanedioic acids and a selectivity of 60% into ethyl monoesters of $C_5$-alkenoic acids, with the diethyl $C_6$-alkanedioates showing a linearity of 61% which means consisting of 61% of diethyl adipate.

EXAMPLES 2-6 AND COMPARATIVE EXAMPLE A

In a similar manner as in Example 1, further experiments were conducted using the alcohol and catalyst components and their amounts as indicated in the Table below. After heating for 15 hours at the indicated temperatures, the GLC analysis, the 1,3-butadiene conversions, the selectivities to diesters, the diester linearity and the selectivities to monoesters mentioned in the Table were observed. The following abbreviations are used in the Table:

BDPbut = 1,4-bis(diphenylphosphino)butane;
BDiPP = 1,3-bis(di-i-propylphosphino)propane;
BcOP = 1,3-bis(c-octylenephosphino)propane (isomeric mixture comprising 1,4- and 1,5-cyclooctylene groups);
BDsBP = 1,3-bis(di-s-butylphosphino)propane;
BDcHP = 1,3-bis(dicyclohexylphosphino)propane;
9-anth. = 9-anthroic acid; DMBZ = 2,6-dimethoxybenzoic acid;
EtOH = ethanol; MeOH = methanol.

TABLE

| Example No. | Alcohol (ml) | 1° Ligand (mmol) | 2° Ligand (mmol) | Anion (mmol) | T °C. | Conv. % | Diester sel. % | Diester lin. % | Monoester sel. % |
|---|---|---|---|---|---|---|---|---|---|
| 1 | EtOH (20) | BDPbut (2.0) | BDiPP (0.6) | 9-anth. (10) | 150 | 100 | 37 | 61 | 60 |
| 2 | EtOH (20) | BDPbut (2.0) | BcOP (0.6) | 9-anth. (10) | 160 | 100 | 80 | 42 | 17 |
| 3 | EtOH (20) | BDPbut (2.0) | BDsBP (0.6) | 9-anth. (10) | 160 | 100 | 42 | 62 | 55 |
| 4 | EtOH (20) | BDPbut (2.0) | BDcHP (0.6) | 9-anth. (10) | 160 | 100 | 46 | 61 | 50 |
| 5 | EtOH (20) | BDPbut (2.0) | BDsBP (0.6) | DMBZ (15) | 160 | 100 | 34 | 60 | 64 |
| 6 | MeOH (15) | BDPbut (2.0) | BDiPP (0.6) | 9-anth. (10) | 160 | 100 | 30 | 67 | 66 |
| A | EtOH (20) | BDPbut (2.0) | — | 9-anth. (10) | 150 | 100 | | trace | 97 |

I claim:

1. A process for the preparation of alkanedioic derivatives comprising reacting an aliphatic conjugated diene with carbon monoxide and a hydroxyl group-containing compound in the presence of a catalyst system comprising:
   a) a source of cationic palladium,
   b) a first bidentate diphosphine ligand having electron-withdrawing substituents on the phosphorus atoms,
   c) a second bidentate diphosphine ligand having electron-releasing substituents on the phosphorus atoms, and
   d) a source of an anion.

2. The process of claim wherein the first bidentate diphosphine ligand comprises aromatic substituents.

3. The process of claim 2 wherein the first bidentate diphosphine ligand is a diphosphine of formula:

$$R^1R^2{>}P{-}R{-}P{<}R^3R^4 \qquad (I)$$

wherein $R^1$, $R^2$, $R^3$ and $R^4$ independently represent optionally substituted aryl groups, and R represents a bridging group having at least two carbon atoms in the bridge.

4. The process of claim wherein the second bidentate diphosphine ligand comprises aliphatic substituents.

5. The process of claim 4 wherein the second bidentate diphosphine ligand is a diphosphine of formula:

$$R^5R^6{>}P{-}R{-}P{<}R^7R^8 \qquad (II),$$

wherein $R^5$, $R^6$, $R^7$ and $R^8$ independently represent optionally substituted aliphatic groups, and R represents a bridging group having at least two carbon atoms in the bridge.

6. The process of claim 5 wherein $R^5$, $R^6$, $R^7$ and $R^8$ are independently selected from the group consisting of alkyl, alkylene, cycloalkyl and cycloalkylene groups.

7. The process of claim wherein the first bidentate diphosphine ligand comprises aromatic substituents and the second bidentate diphosphine ligand comprises aliphatic substituents.

8. The process of claim 7 wherein the aliphatic conjugated diene is 1,3-butadiene.

9. The process of claim 7 wherein the hydroxyl group-containing compound is an alkanol having from 1 to 6 carbon atoms.

* * * * *